(12) United States Patent
Chang

(10) Patent No.: US 8,720,444 B2
(45) Date of Patent: May 13, 2014

(54) BREATHING ASSISTANCE APPARATUS HAVING FLOATING FUNCTION

(75) Inventor: Eric Chang, Taichung (TW)

(73) Assignee: Hsiner Co., Ltd., Taichung (TW)

( * ) Notice: Subject to any disclaimer, the term of this patent is extended or adjusted under 35 U.S.C. 154(b) by 338 days.

(21) Appl. No.: 13/354,473

(22) Filed: Jan. 20, 2012

(65) Prior Publication Data

US 2013/0186403 A1   Jul. 25, 2013

(51) Int. Cl.
*A61M 16/06* (2006.01)

(52) U.S. Cl.
CPC ........... *A61M 16/0666* (2013.01); *A61M 16/06* (2013.01)
USPC ............ 128/207.13; 128/206.21; 128/206.24; 128/205.25

(58) Field of Classification Search
CPC ........... A61M 16/06; A61M 16/0683; A61M 16/0666; A61M 2210/0618; A61M 2016/0616; A61M 2016/0622; A61M 2016/0661; A61M 2016/0611
USPC ............. 128/200.24, 200.26, 204.18, 205.25, 128/206.21, 206.24, 206.28, 207.13, 207.18
See application file for complete search history.

(56) References Cited

U.S. PATENT DOCUMENTS

| | | | |
|---|---|---|---|
| 6,431,172 B1 * | 8/2002 | Bordewick | 128/207.18 |
| 7,201,169 B2 * | 4/2007 | Wilkie et al. | 128/207.18 |
| 7,287,528 B2 * | 10/2007 | Ho et al. | 128/206.21 |
| 7,640,934 B2 * | 1/2010 | Zollinger et al. | 128/207.18 |
| 7,726,309 B2 * | 6/2010 | Ho et al. | 128/204.18 |
| 7,931,024 B2 * | 4/2011 | Ho et al. | 128/206.21 |
| 7,975,694 B2 * | 7/2011 | Ho | 128/207.13 |
| 7,987,850 B2 * | 8/2011 | Zollinger et al. | 128/206.11 |
| 8,267,089 B2 * | 9/2012 | Ho et al. | 128/206.21 |
| 8,291,905 B2 * | 10/2012 | Moenning, Jr. | 128/206.21 |
| 8,297,283 B2 * | 10/2012 | Hitchcock et al. | 128/206.24 |
| 8,312,881 B2 * | 11/2012 | Gunaratnam et al. | 128/206.24 |
| 8,402,971 B2 * | 3/2013 | Scheiner et al. | 128/206.24 |
| 8,479,737 B2 * | 7/2013 | Moenning, Jr. | 128/206.21 |
| 8,631,792 B2 * | 1/2014 | Ho et al. | 128/206.24 |
| 2003/0200970 A1 * | 10/2003 | Stenzler et al. | 128/207.18 |
| 2004/0118406 A1 * | 6/2004 | Lithgow et al. | 128/206.24 |
| 2004/0144386 A1 * | 7/2004 | Frater et al. | 128/206.24 |
| 2007/0125387 A1 * | 6/2007 | Zollinger et al. | 128/207.18 |
| 2007/0277828 A1 * | 12/2007 | Ho et al. | 128/206.21 |
| 2010/0122705 A1 * | 5/2010 | Moenning, Jr. | 128/206.24 |
| 2010/0199992 A1 * | 8/2010 | Ho et al. | 128/205.25 |
| 2011/0162655 A1 * | 7/2011 | Gunaratnam et al. | 128/207.18 |
| 2013/0133664 A1 * | 5/2013 | Startare et al. | 128/206.24 |

* cited by examiner

*Primary Examiner* — Annette Dixon
(74) *Attorney, Agent, or Firm* — Muncy, Geissler, Olds & Lowe, P.C.

(57) ABSTRACT

A breathing assistance apparatus includes a main body unit, a head strap unit, a nasal prong unit, and an intake unit. The main body unit has a rearwall, a frontwall, a connecting wall connected between the rearwall and the frontwall to define a chamber thereamong. The connecting wall has a rearwall-connecting portion connected to the rearwall, and a frontwall-connecting portion connected between the frontwall and the rearwall-connecting portion and having a thickness smaller than that of the rearwall-connecting portion so as to allow for floating movement of the frontwall relative to the rearwall.

6 Claims, 6 Drawing Sheets

BREATHING ASSISTANCE APPARATUS HAVING FLOATING FUNCTION

BACKGROUND OF THE INVENTION

1. Field of the Invention

This invention relates to medical supplies, and more particularly to a breathing assistance apparatus that includes a nasal prong unit and that is adapted to deliver gases to a patient.

2. Description of the Related Art

Referring to FIGS. 1 and 2, a conventional breathing assistance apparatus includes a main body 1, a head strap 2 connected to two sides of the main body 1, a nasal prong 3 disposed behind and connected to the main body 1, and an intake tube 4 disposed in front of and connected to the main body 1. The main body 1 is made of silicone gel, and has a rearwall 101 and a frontwall 102 extending forwardly and convergently from a periphery of the rearwall 101. The rearwall 101 has an insert hole 103 permitting insertion of the nasal prong 3. The frontwall 102 has a coupling hole 104 permitting the intake tube 4 to be mounted thereinto.

When the user sleeps and wears the breathing assistance apparatus, and when an external force is applied to the intake tube 4, the intake tube 4 drives movement of the main body 1 and the nasal prong 3. Hence, the nasal prong 3 may separate from the nose of the user to result in insufficient gas supply, thereby affecting adversely the sleeping quality of the user.

SUMMARY OF THE INVENTION

The object of this invention is to provide a breathing assistance apparatus that has floating function so as not to separate from the nose of the user during sleeping, thereby ensuring normal gas supply.

According to this invention, there is provided a breathing assistance apparatus comprising:

a main body unit having a rearwall, a frontwall, a connecting wall connected between the rearwall and the frontwall to define a chamber thereamong, the rearwall having an insert hole in fluid communication with the chamber, the frontwall having a coupling hole in fluid communication with the chamber, the connecting wall having a rearwall-connecting portion connected to the rearwall, and a frontwall-connecting portion connected between the frontwall and the rearwall-connecting portion, the frontwall-connecting portion having a thickness smaller than that of the rearwall-connecting portion so as to allow for floating movement of the frontwall relative to the rearwall;

a head strap unit connected to the main body unit;

a nasal prong unit including a main plate inserted into the main body unit and aligned with the insert hole, and two nasal prongs disposed on the main plate; and an intake unit mounted to the main body unit and extending into the coupling hole in the main body unit.

As such, since the frontwall can float relative to the rearwall, when an external force is applied to the intake unit, undesired removal of the nasal prongs from the nostrils of the user can be prevented during sleeping, so that the sleeping quality of the user can be improved.

BRIEF DESCRIPTION OF THE DRAWINGS

These and other features and advantages of this invention will become apparent in the following detailed description of a preferred embodiment of this invention, with reference to the accompanying drawings, in which.

DETAILED DESCRIPTION OF THE PREFERRED EMBODIMENT

Figure 1:
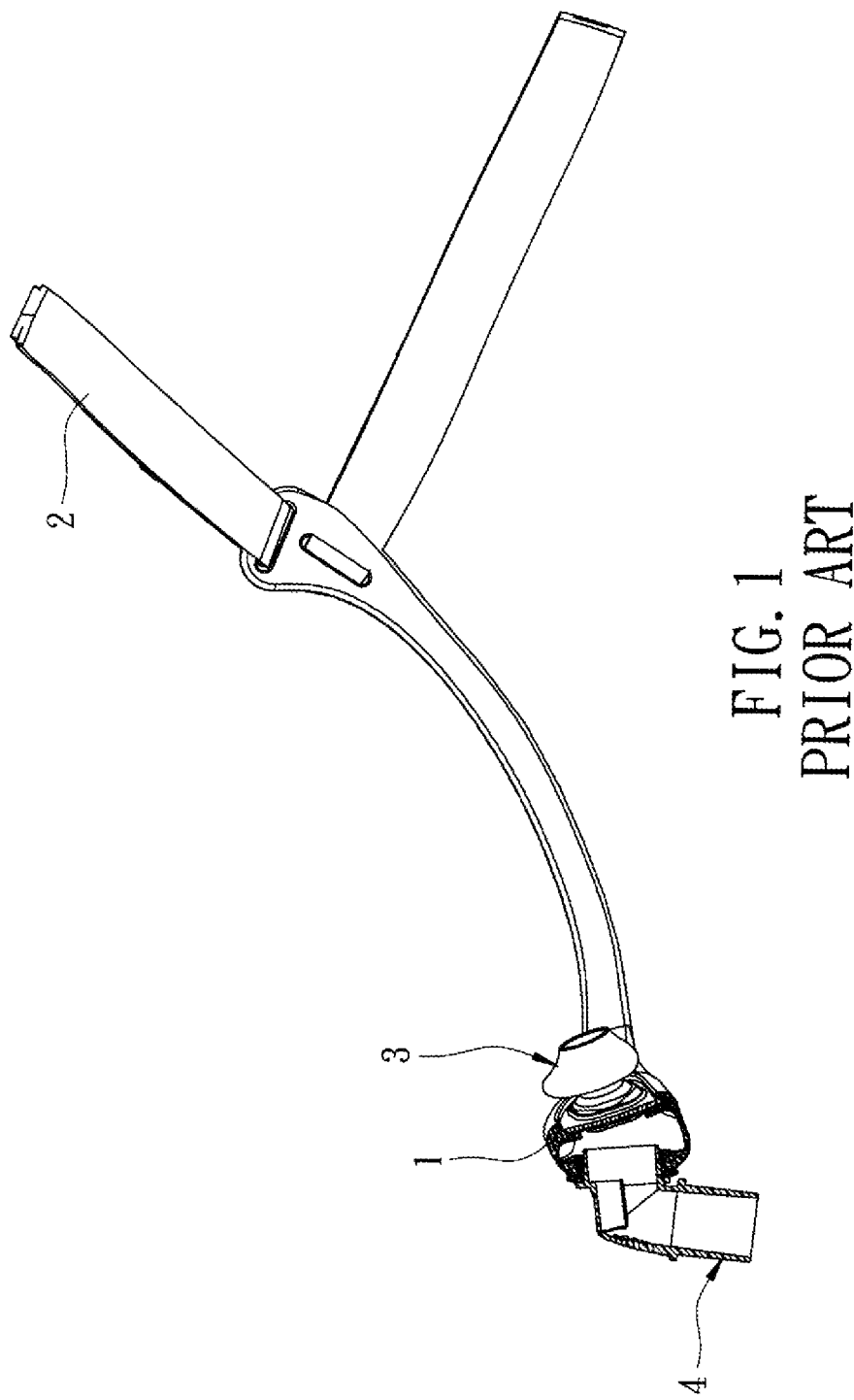
FIG. 1 is a fragmentary schematic view of a conventional breathing assistance apparatus.
Figure 2:
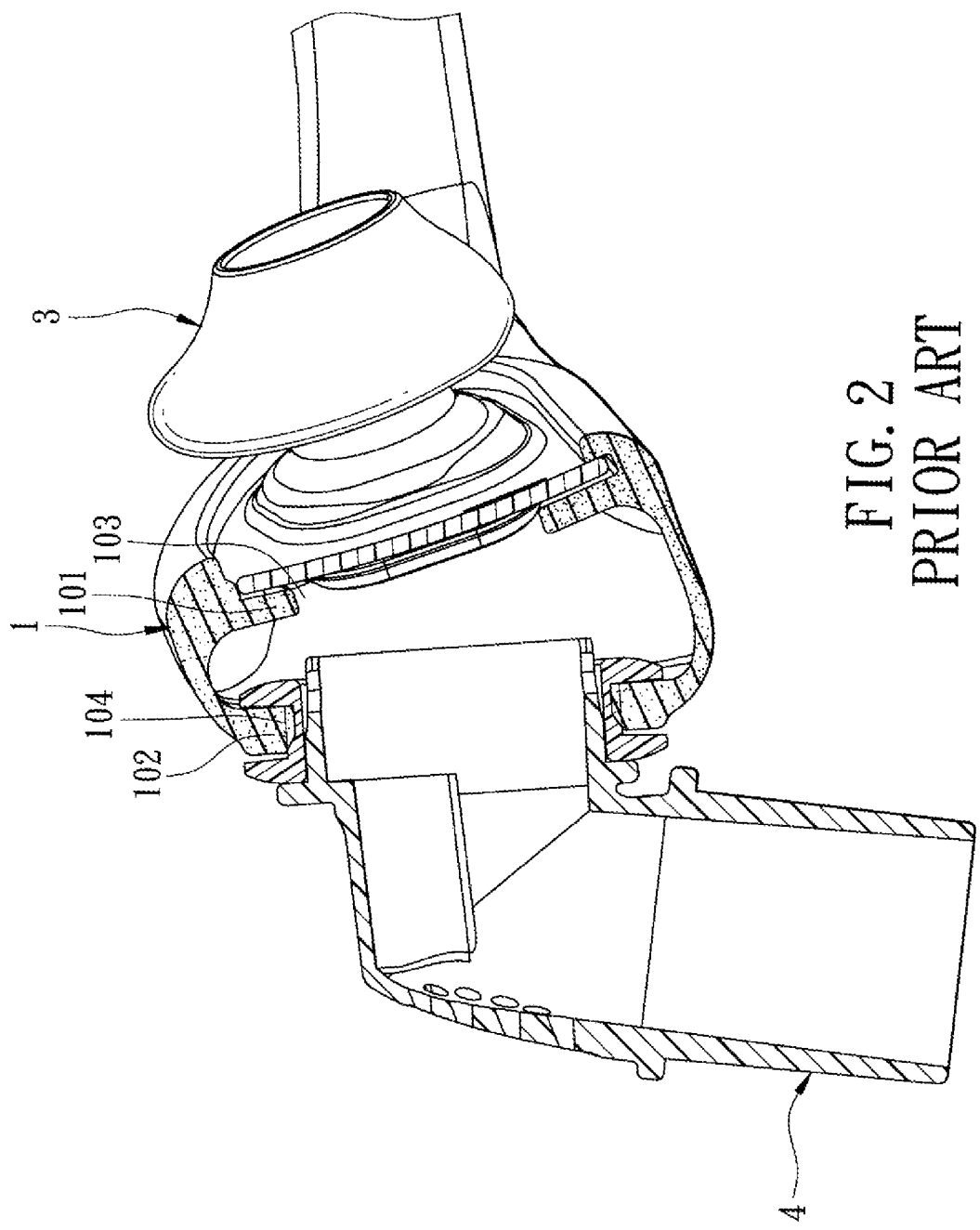
FIG. 2 is an enlarged view of a portion of FIG. 1.
Figure 3:
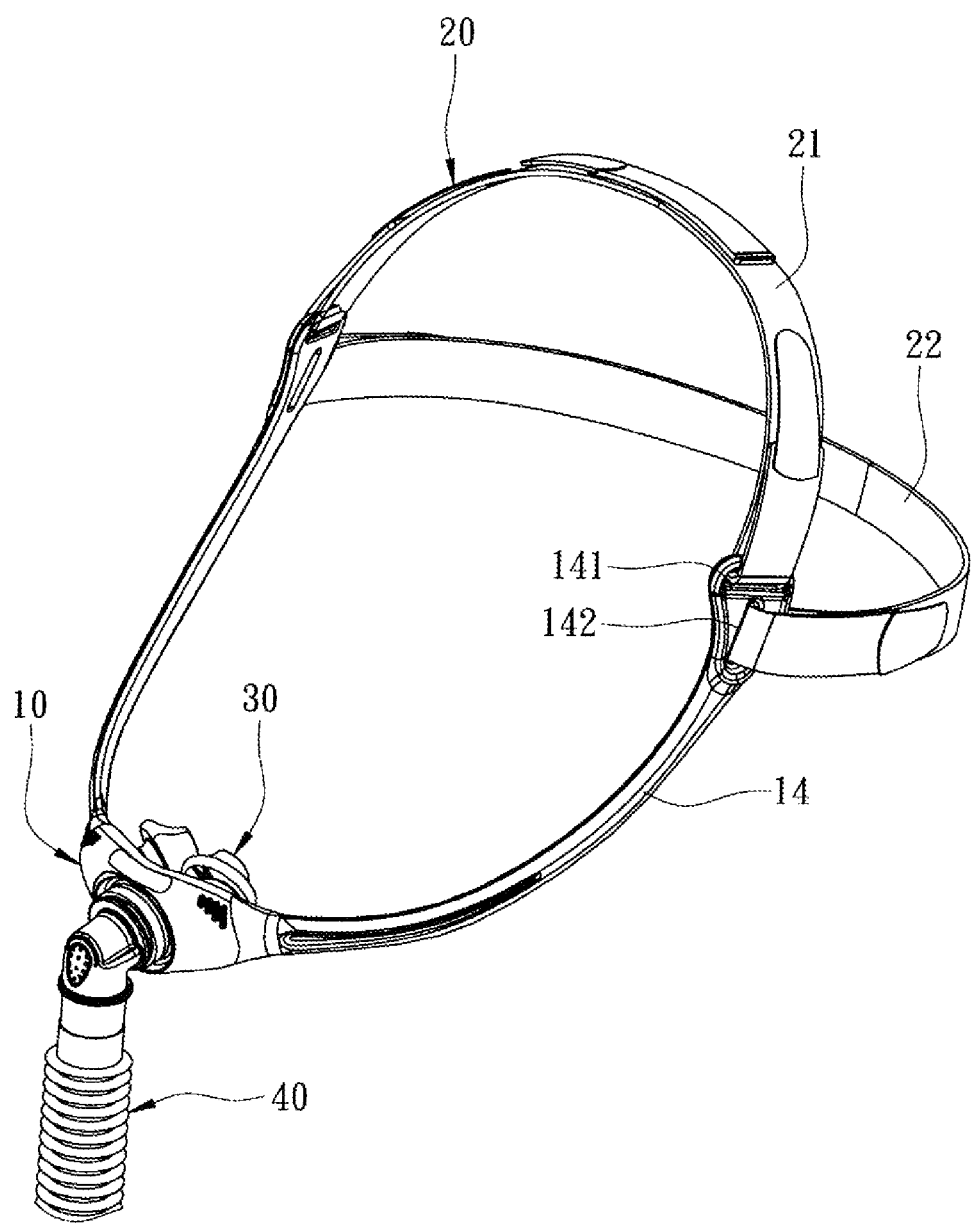
FIG. 3 is a perspective view of the preferred embodiment of a breathing assistance apparatus according to this invention.

Referring to FIGS. 2 and 3, the first preferred embodiment of a breathing assistance apparatus according to this invention includes a main body unit 10, a head strap unit 20, a nasal prong unit 30, and an intake unit 40.

The main body unit 10 is made of silicone gel, and has a rearwall 11, a frontwall 12, a connecting wall 13 connected between the rearwall 11 and the frontwall 12, and two side straps 14 connected to the rearwall 11. The frontwall 11 cooperates with the rearwall 12 and the connecting wall 13 to define a chamber 15 thereamong. The rearwall 11 has an insert hole 111 in fluid communication with the chamber 15, and a first insert groove 112 disposed behind the insert hole 111 and having a width reducing rearwardly. The frontwall 12 has a coupling hole 121 defined by an annular inner surface 122, and an annular second insert groove 123 formed in the inner surface 122. The coupling hole 121 is in fluid communication with the chamber 15. The connecting wall 13 has a rearwall-connecting portion 131 connected to the rearwall 11, and a frontwall-connecting portion 132 connected between the frontwall 12 and the rearwall-connecting portion 131. The frontwall-connecting portion 132 has a thickness smaller than that of the rearwall-connecting portion 131 so as to allow for floating movement of the frontwall 12 relative to the rearwall 11. The frontwall-connecting portion 132 is formed with a rearwardly extending annular projection 133 and a forwardly opening annular groove 134 aligned with the annular projection 133 in a front-to-rear direction, such that it is U-shaped in cross-section. Alternatively, the frontwall-connecting portion 132 may be formed with two rearwardly extending annular projections 133 and two forwardly opening annular grooves 134. Each of the side straps 14 has an end portion formed with a first through hole 141 and a second through hole 142.

The head strap unit 20 is connected to the side straps 14 of the main body unit 10, and has a first head strap 21 extending through the first through holes 141 in the side straps 14, and a second head strap 22 extending through the second through holes 142 in the side straps 14.

The nasal prong unit 30 includes a main plate 31 inserted into the main body unit 10 and aligned with the insert hole 111, and two nasal prongs 32 disposed on the main plate 31. In this embodiment, the main plate 31 is confined within the first insert groove 112, and has two mounting holes 311. The nasal prongs 32 are made of silicone gel, and are hollow. Each of the nasal prongs 32 has an insert barrel 321 inserted into the corresponding mounting hole 311, and a nostril-engaging plug 322 adapted to be inserted into one nostril of the user.

The intake unit 40 is mounted to the main body unit 10, extends into the coupling hole 121, and is opposite to the nasal prong unit 30. In this embodiment, the intake unit 40 includes a tube-sleeving member 41 inserted into the coupling hole 121, and an intake tube 42 having an end permitting the tube-sleeving member 41 to be sleeved fixedly thereon. The tube-sleeving member 41 includes a tubular body 410 and an annular flange 411 extending radially and outwardly from the tubular body 410 and engaging rotatably the second insert groove 123.

Figure 4:
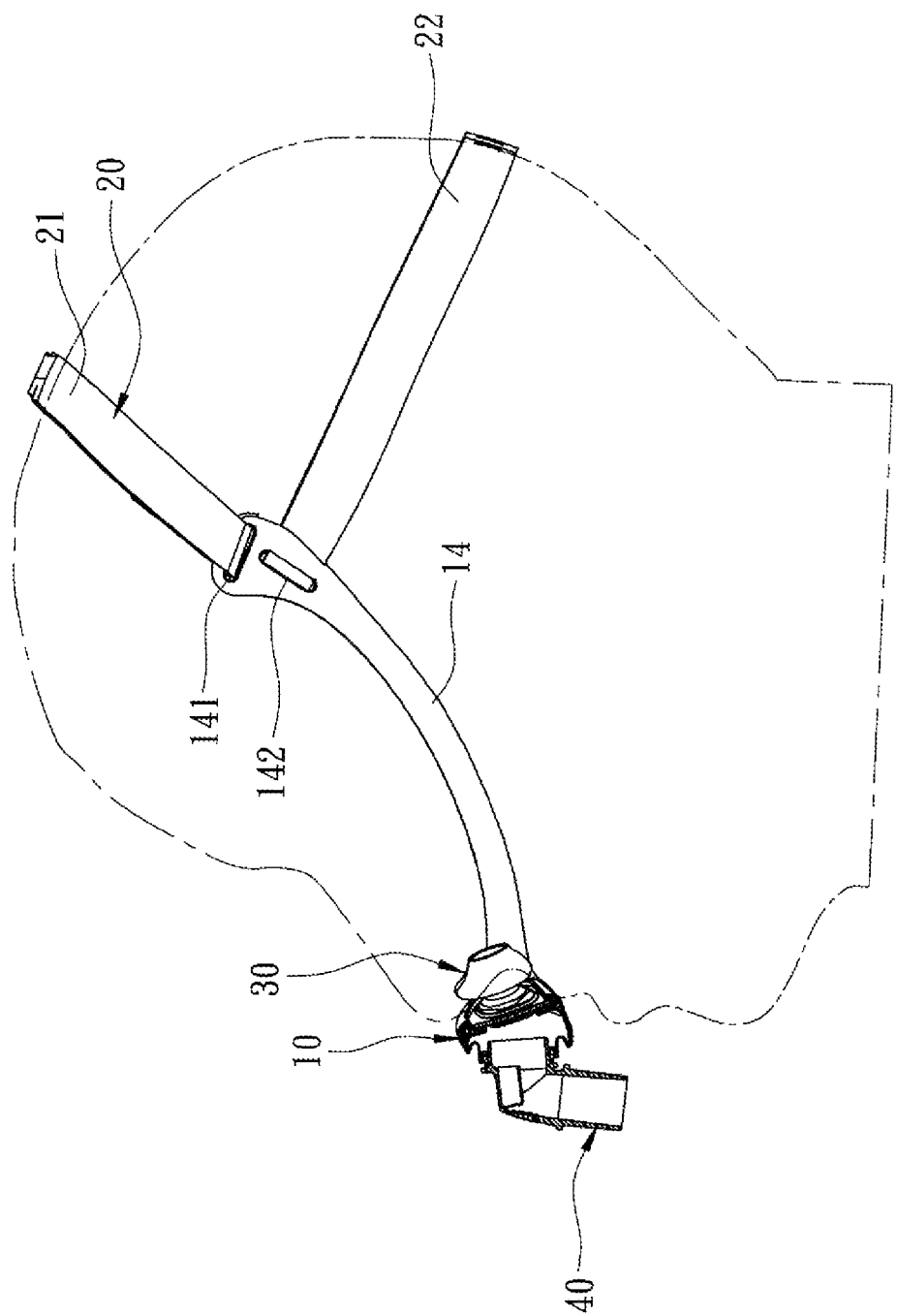
FIG. 4 is a schematic view illustrating how to use the preferred embodiment.
Figure 5:
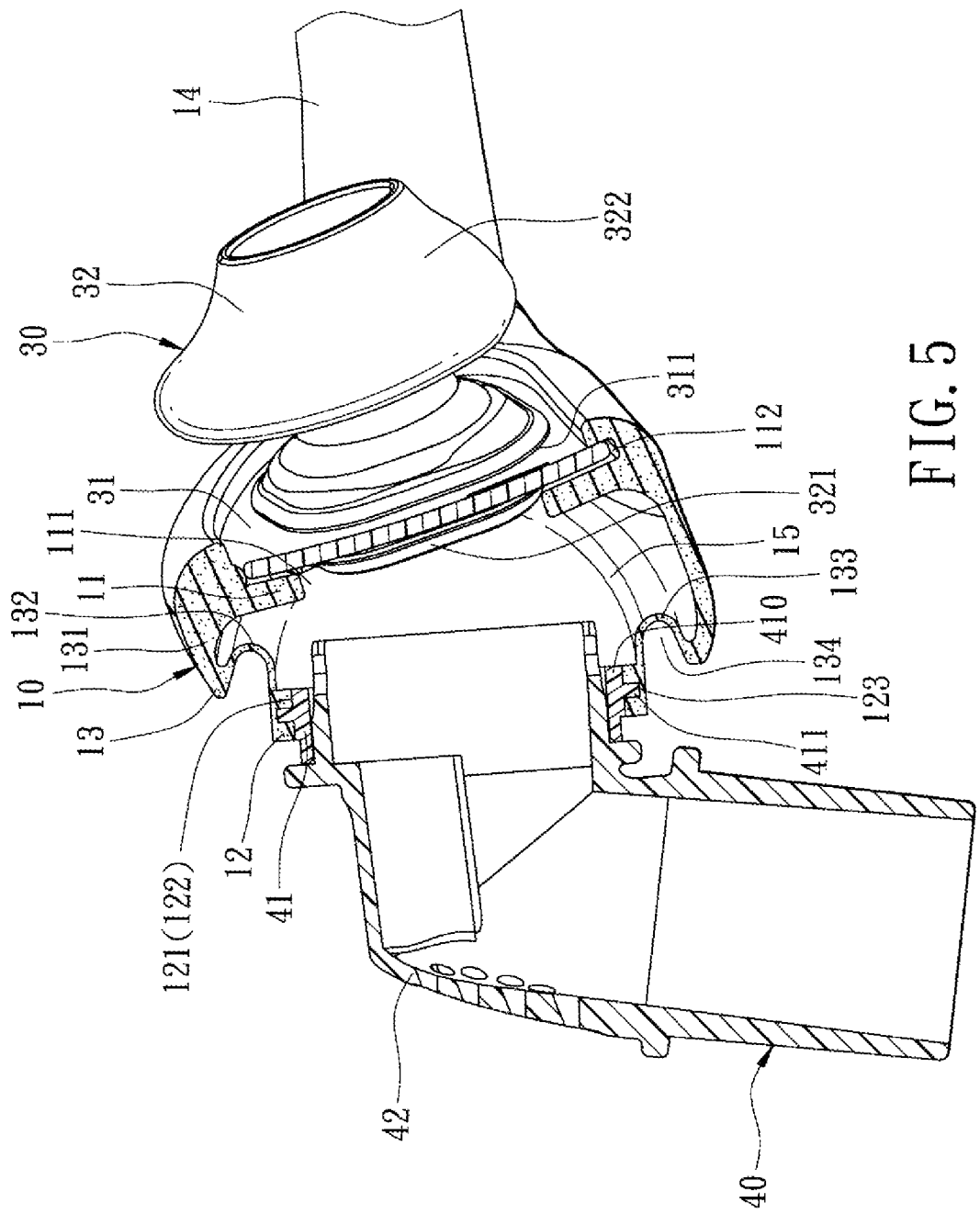
FIG. 5 is an enlarged view of a portion of FIG. 4.

With further reference to FIGS. 4 and 5, during use, the nostril-engaging plugs 322 of the nasal prongs 32 are inserted respectively into the nostrils of the user, and an assembly of the first head strap 21 and the main body unit 10 is sleeved on the head of the user, in such a manner that the first head strap 21 is adjusted in length to press against a top end of the head of the user in a known manner. Subsequently, the second head strap 22 is adjusted in length to press against a rear side of the head of the user.

Figure 6:
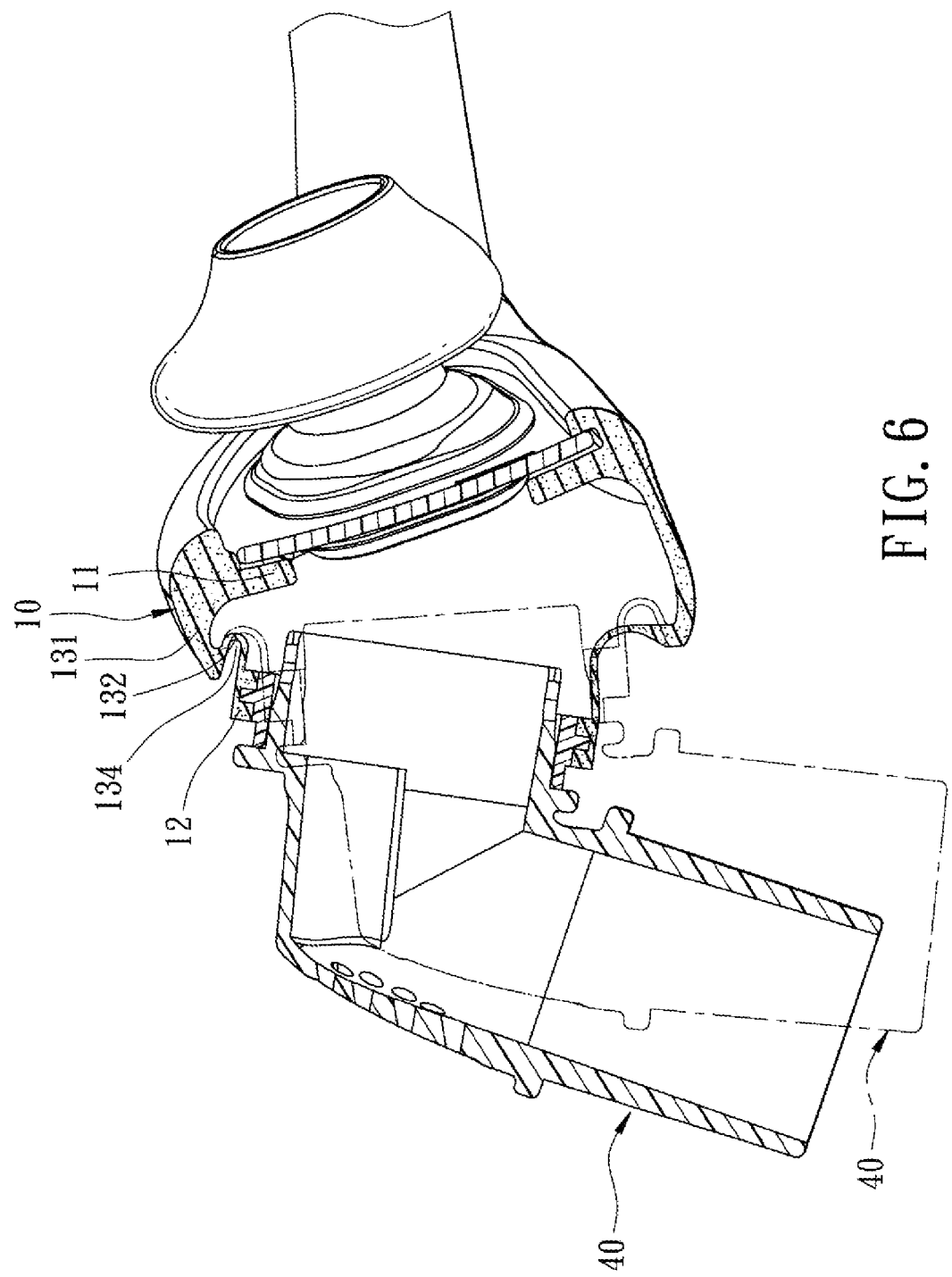
FIG. 6 is a schematic, partly sectional view of the preferred embodiment, illustrating movement of an intake tube.

Referring to FIG. 6, when the user sleeps and wears the breathing assistance apparatus, and when an external force is applied to the intake unit 40 to move the frontwall 12, since the thickness of the frontwall-connecting portion 132 is smaller than that of the rearwall-connecting portion 131, the frontwall-connecting portion 132 is deformed from a shape shown by the phantom lines to a shape shown by the solid lines, in such a manner that the frontwall 12 is moved relative to the rearwall 11. As a result, the nostril-engaging plugs 322 of the nasal prongs 32 remain in the nostrils of the user, so as to allow for normal gas supply of the breathing assistance apparatus. Thus, the object of this invention is achieved.

With this invention thus explained, it is apparent that numerous modifications and variations can be made without departing from the scope and spirit of this invention. It is therefore intended that this invention be limited only as indicated by the appended claims.

I claim:

1. A breathing assistance apparatus comprising:
a main body unit having a rearwall, a frontwall, a connecting wall connected between said rearwall and said frontwall to define a chamber thereamong, said rearwall having an insert hole in fluid communication with said chamber, said frontwall having a coupling hole in fluid communication with said chamber, said connecting wall having a rearwall-connecting portion connected to said rearwall, and a frontwall-connecting portion connected between said frontwall and said rearwall-connecting portion, said frontwall-connecting portion having a thickness smaller than that of said rearwall-connecting portion so as to allow for floating movement of said frontwall relative to said rearwall;
a head strap unit connected to said main body unit;
a nasal prong unit including a main plate inserted into said main body unit and aligned with said insert hole, and two nasal prongs disposed on said main plate; and
an intake unit mounted to said main body unit and extending into said coupling hole in said main body unit.

2. The breathing assistance apparatus as claimed in claim 1, wherein said frontwall-connecting portion is formed with at least one rearwardly extending annular projection and at least one forwardly opening annular groove aligned with said annular projection in a front-to-rear direction.

3. The breathing assistance apparatus as claimed in claim 2, wherein said frontwall-connecting portion is U-shaped in cross-section.

4. The breathing assistance apparatus as claimed in claim 1, wherein said rearwall of said main body unit further has a first insert groove disposed behind said insert hole and having a width reducing rearwardly, said main plate of said nasal prong unit being confined within said first insert groove.

5. The breathing assistance apparatus as claimed in claim 4, wherein said frontwall of said main body unit further has an annular inner surface defining said coupling hole and formed with an annular second insert groove, said intake unit including a tube-sleeving member inserted into said coupling hole, and an intake tube having an end permitting said tube-sleeving member to be sleeved fixedly thereon, said tube-sleeving member including a tubular body and an annular flange extending radially and outwardly from said tubular body and engaging rotatably said second insert groove.

6. The breathing assistance apparatus as claimed in claim 1, wherein said main body unit is made of silicone gel, and further has two side straps connected to said rearwall, said head strap unit having a first head strap and a second head strap, each of which is connected between said side straps.

* * * * *